US011376055B2

(12) United States Patent
Wogoman et al.

(10) Patent No.: US 11,376,055 B2
(45) Date of Patent: Jul. 5, 2022

(54) SYSTEM AND METHOD FOR ATTACHING A SURGICAL INSTRUMENT TO A PATIENT'S BONE

(71) Applicant: DePuy Ireland Unlimited Company, Ringaskiddy (IE)

(72) Inventors: Thomas E. Wogoman, Warsaw, IN (US); Rusty T. Meier, Warsaw, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 277 days.

(21) Appl. No.: 16/835,706

(22) Filed: Mar. 31, 2020

(65) Prior Publication Data
US 2020/0222101 A1    Jul. 16, 2020

Related U.S. Application Data

(62) Division of application No. 14/674,757, filed on Mar. 31, 2015, now Pat. No. 10,603,094.

(51) Int. Cl.
| A61B 17/88 | (2006.01) |
| A61B 17/86 | (2006.01) |
| A61B 17/15 | (2006.01) |
| A61B 90/00 | (2016.01) |
| A61B 17/56 | (2006.01) |

(52) U.S. Cl.
CPC ........ *A61B 17/8891* (2013.01); *A61B 17/862* (2013.01); *A61B 17/8883* (2013.01); *A61B 17/15* (2013.01); *A61B 17/155* (2013.01); *A61B 17/8645* (2013.01); *A61B 2017/564* (2013.01); *A61B 2090/033* (2016.02)

(58) Field of Classification Search
CPC .......................... A61B 17/862; A61B 17/8891
See application file for complete search history.

(56) References Cited

U.S. PATENT DOCUMENTS

| 5,431,660 A * | 7/1995 | Burke ................ A61B 17/8685 411/536 |
| 5,901,622 A | 5/1999 | Sweeny |
| 9,597,785 B1 | 3/2017 | Gertner |
| 10,603,094 B2 | 3/2020 | Wogoman et al. |
| 2004/0243139 A1 | 12/2004 | Lewis et al. |

(Continued)

FOREIGN PATENT DOCUMENTS

| CN | 202223334 U | 5/2012 |
| DE | 102009033138 A1 | 2/2011 |

(Continued)

OTHER PUBLICATIONS

European Search Report for Application No. 16160726.2, dated Oct. 5, 2016, 11 pages.

(Continued)

*Primary Examiner* — Samuel S Hanna
(74) *Attorney, Agent, or Firm* — Barnes & Thornburg LLP

(57) ABSTRACT

A surgical instrument system and method of use is disclosed. The system includes a bone fixation pin and a surgical instrument configured for use with the bone fixation pin. The surgical instrument includes a sheath extending over the distal end of an elongated shaft and a locking mechanism operable to permit selectively movement of the elongated shaft along the longitudinal axis relative to the sheath.

5 Claims, 10 Drawing Sheets

(56) References Cited

U.S. PATENT DOCUMENTS

| | | |
|---|---|---|
| 2005/0065410 A1 | 3/2005 | Bjork et al. |
| 2006/0079903 A1 | 4/2006 | Wong |
| 2007/0106283 A1 | 5/2007 | Garcia et al. |
| 2014/0358186 A1 | 12/2014 | Frock et al. |
| 2015/0101177 A1 | 4/2015 | Hall et al. |

FOREIGN PATENT DOCUMENTS

| | | |
|---|---|---|
| EP | 3655224 A1 | 5/1995 |
| EP | 2777574 A1 | 9/2014 |

OTHER PUBLICATIONS

Partial European Search Report for Application No. 16160726.2, dated Jun. 24, 2016, 7 pages.
Chinese Search Report, Chinese Application No. 201610195759.9, dated Oct. 28, 2019, 15 pages.
Japanese Office Action for Japanese Application No. 2016-067552, dated Dec. 24, 2019, 5 pages.

\* cited by examiner

SYSTEM AND METHOD FOR ATTACHING A SURGICAL INSTRUMENT TO A PATIENT'S BONE

This application is a divisional application and claims priority to U.S. patent application Ser. No. 14/674,757, now U.S. Pat. No. 10,603,094, which was filed on Mar. 31, 2015, the entirety of which is expressly incorporated herein by reference.

TECHNICAL FIELD

The present disclosure relates generally to orthopaedic surgical instruments and, more particularly, to surgical instruments used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments.

SUMMARY

According to one aspect of the disclosure, a surgical instrument system is disclosed. The surgical instrument system comprises a bone fixation pin including a head and a shaft extending from the head to a distal end having a plurality of threads defined therein, and a surgical instrument configured for use with the bone fixation pin. The surgical instrument comprises an elongated shaft defining a longitudinal axis extending through its proximal end and its distal end, a socket defined in the distal end of the elongated shaft that is sized to receive the head of the bone fixation pin, a shank extending outwardly from the proximal end of the elongated shaft along the longitudinal axis that is configured to engage a surgical drill, a sheath extending over the distal end of the elongated shaft, and a locking mechanism coupled to the elongated shaft. The locking mechanism is operable to permit selectively movement of the elongated shaft along the longitudinal axis relative to the sheath between a position in which over-turning or over-torqueing the bone fixation pin is prevented and another position in which full torque may be applied to the bone fixation pin for final tightening or removal of the pin from the bone. In that way, the torque applied to the bone fixation pin may be controlled.

In some embodiments, the locking mechanism may include a locking tab that is moveable between a locked position in which the locking tab is positioned in an opening of the sheath to prevent movement of the elongated shaft and an unlocked position in which the locking tab is spaced apart from the opening to permit movement of the elongated shaft.

In some embodiments, the locking mechanism may include a body that is positioned in a slot defined in the elongated shaft, and the locking tab may extend outwardly from the body. Additionally, in some embodiments, the body may include a biasing element that biases the locking tab in the locked position. In some embodiments, the slot defined in the elongated shaft may extend longitudinally through the elongated shaft.

In some embodiments, the body may include a first end engaged with an inner surface of the sheath. When the locking tab is in the locked position, a second end of the body may be engaged with a distal-facing surface of the elongated shaft. When the locking tab is in the unlocked position, the second end of the body may be disengaged from the distal-facing surface of the elongated shaft.

In some embodiments, the first end of the body may be received in a groove defined in the inner surface of the sheath. In some embodiments, the sheath may include a distal opening defined in its distal end and a central passageway that extends inwardly from the distal opening. The elongated shaft may be positioned in the central passageway of the sheath. When the elongated shaft is moved in a first direction relative to the sheath, the distal end of the elongated shaft may be moved along the central passageway toward the distal end of the sheath.

In some embodiments, the head of the bone fixation pin may extend from a proximal end of the bone fixation pin to a distal edge. The threads of the shaft may extend from the distal end to a proximal edge, and a first distance may be defined between the distal edge of the head and the proximal edge of the threads. When the elongated shaft is located in a first position relative to the sheath, a second distance may be defined between the distal opening of the sheath and the distal end of the elongated shaft. The second distance may be greater than the first distance such that a number of the threads of the bone fixation pin are positioned in the central passageway of the sheath when the head of the bone fixation pin is fully seated in the socket of the elongated shaft.

In some embodiments, the elongated shaft may be moveable to a second position in which a third distance is defined between the opening of the sheath and the distal end of the elongated shaft. The third distance may be less than the first distance.

In some embodiments, the locking mechanism may be biased in a locked position in which the elongated shaft is prevented from moving relative to the sheath when the elongated shaft is in the first position. Additionally, the locking mechanism may be in an unlocked position in which the elongated shaft is permitted to move relative to the sheath when the elongated shaft is the second position.

Additionally, in some embodiments, the elongated shaft may include a pair of tabs extending outwardly from its proximal end and the sheath includes a pair of guide slots that receive the pair of tabs. The guide slots and the tabs may cooperate to prevent rotational movement about the longitudinal axis. In some embodiments, the socket and the head of the bone fixation pin may have corresponding triangular cross sections.

According to another aspect, a method of attaching a surgical instrument to a patient's bone is disclosed. The method comprises positioning the surgical instrument in a desired location relative to the patient's bone, inserting a head of a bone fixation pin through a distal opening of a fixation pin driver into a socket defined in an elongated shaft of the fixation pin driver, positioning a threaded distal end of the bone fixation pin in a guide hole defined in the surgical instrument, rotating the fixation pin driver to thread the bone fixation pin into the patient's bone, engaging a distal end of the fixation pin driver with an outer surface of the surgical instrument, operating a locking mechanism of the fixation pin driver to release the elongated shaft of the fixation pin driver for movement relative to an outer sheath of the fixation pin driver that includes the distal end of the driver, and rotating the fixation pin driver and advancing the socket of the fixation pin driver toward the distal opening of the fixation pin driver to further thread the bone fixation pin into the patient's bone.

In some embodiments, the method may further comprise securing a proximal end of the elongated shaft to a surgical drill. In some embodiments, the surgical instrument may be a cutting guide block.

In some embodiments, the method may further comprise engaging an annular flange of the bone fixation pin with the outer surface of the surgical instrument after advancing the socket of the fixation pin driver toward the distal opening of the fixation pin driver. Additionally, in some embodiments, the method may further comprise moving the socket of the fixation pin driver away the distal opening of a fixation pin driver until a biasing element causes the locking mechanism to engage the outer sheath and prevent movement of the elongated shaft.

According to another aspect, a surgical instrument system comprises a bone fixation pin including a head extending from a proximal end of the bone fixation pin to a distal edge, and a shaft extending from the head to a distal end having a plurality of threads defined therein that extend from the distal end to a proximal edge. The system also includes a surgical instrument configured for use with the bone fixation pin. The surgical instrument comprises a socket sized to receive the head of the bone fixation pin and a sheath extending over the socket to a distal end. A first distance is defined between the distal edge of the head and the proximal edge of the threads of the bone fixation pin, and the socket is moveable between a plurality of positions relative to the sheath. The plurality of positions includes a first position in which a second distance is defined between the distal end of the sheath and the socket such that a number of the threads of the bone fixation pin are positioned in the sheath when the head of the bone fixation pin is fully seated in the socket. In some embodiments, the socket may be moveable to a second position in which a third distance is defined between the distal end of the sheath and the socket. The third distance may be less than the first distance.

BRIEF DESCRIPTION OF THE DRAWINGS

The detailed description particularly refers to the following figures, in which.

DETAILED DESCRIPTION OF THE DRAWINGS

Figure 1:
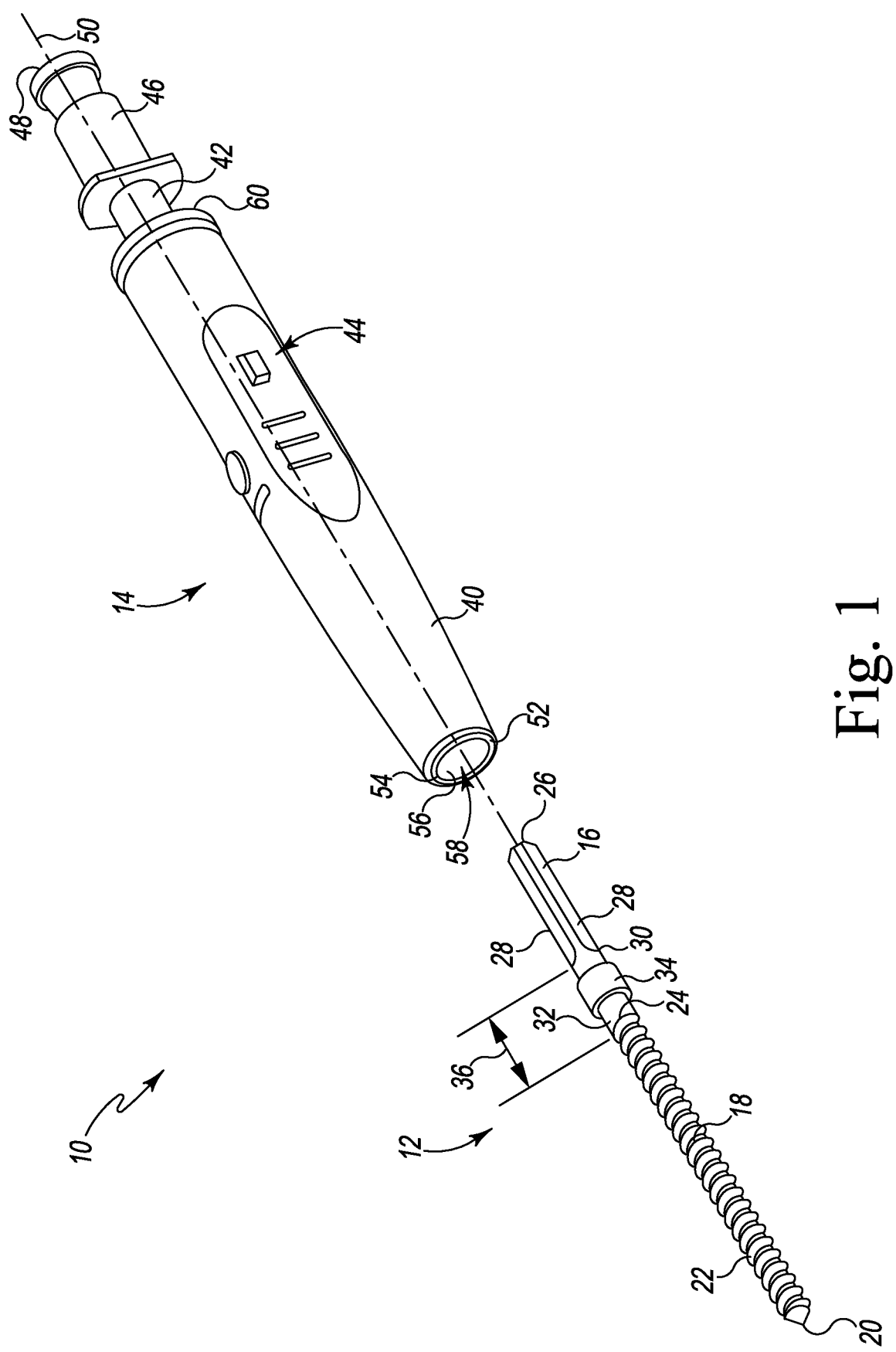
FIG. 1 is a perspective view of a surgical instrument system for attaching a surgical instrument to a patient's bone.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, a surgical instrument system 10 for attaching a surgical instrument to a patient's bone is shown. The system 10 includes a bone fixation pin 12 and a fixation pin driver 14 configured to be attached to the head 16 of the fixation pin 12. As described in greater detail below, the driver 14 is operable to control the torque applied to the fixation pin 12.

The fixation pin 12 includes an elongated shaft 18 that extends distally from the head 16 to a distal tip 20 of the pin 12. In the illustrative embodiment, the pin 12 is formed as a single, monolithic component from a metallic material such as, for example, stainless steel. In other embodiments, the head 16 and shaft 18, for example, might be formed as separate components. A plurality of threads 22 are defined in the elongated shaft 18 and extend from the distal tip 20 to a proximal edge 24. The threads 22 are configured to grip the patient's bone to hold the pin 12 (hence the surgical instrument) in position on the bone.

The head 16 of the fixation pin 12 is positioned at a proximal end 26 of the pin 12. The head 16 includes a number of substantially planar surfaces 28 that extend distally from the proximal end 26 to a distal edge 30. In the illustrative embodiment, the surfaces 28 define a generally triangular-shape; in other embodiments, the surfaces 28 may define, for example, a generally square shape.

The elongated shaft 18 includes a substantially smooth surface 32 that connects the proximal edge 24 of the threads 22 to the distal edge 30 of the head 16. The fixation pin 12 also includes an annular flange 34 that extends outwardly from the surface 32. As shown in FIG. 1, a distance 36 is defined between the distal edge 30 and the proximal edge 24.

The driver 14 includes a sheath 40 that extends over an elongated shaft 42. The shaft 42 is moveable relative to the sheath 40, but the driver 14 includes a locking mechanism 44 operable to fix the sheath 40 and the shaft 42 in position relative to one another. The shaft 42 has a drive shank 46 formed at its proximal end 48. The shank 46 is configured to engage a surgical drill or other rotary tool operable to rotate the driver 14 about its longitudinal axis 50. As shown in FIG. 1, the longitudinal axis 50 extends through the proximal end 48 of the shaft 42 and the distal end 52 of the sheath 40.

An opening 54 is defined in the distal end 52 of the sheath 40, and a cylindrical inner wall 56 extends inwardly from the opening 54. The inner wall 56 defines a central passageway 58 that extends through the distal end 52 and opposite proximal end 60 of the sheath 40. The elongated shaft 42 extends outwardly from the proximal end 60 of the sheath 40 to its proximal end 48.

Figure 2:
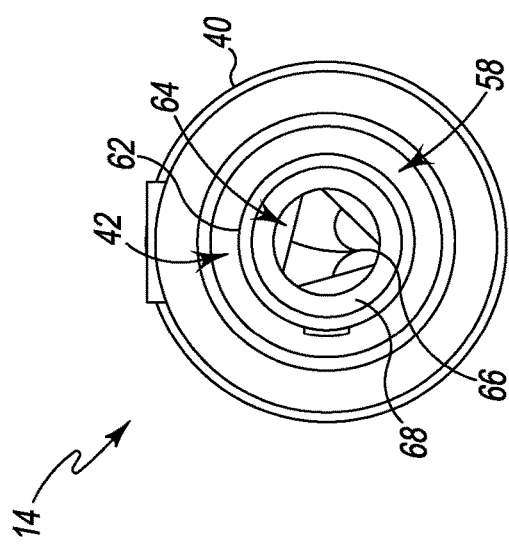
FIG. 2 is an elevation view of a distal end of a surgical instrument of the system of FIG. 1.

As shown in FIG. 2, the distal end 62 of the elongated shaft 42 is positioned in the central passageway 58. A socket 64 sized to receive the head 16 of the fixation pin 12 is defined in the distal end 62 of the shaft 42. The socket 64 has a number of substantially planar surfaces 66 that extend inwardly from an annular beveled surface 68. The surfaces 66 correspond in shape and arrangement to the surfaces 28 of the head 16 such that the head 16 may be snuggly in the socket 64. The socket 64 is sized so that the head 16 fully seats in the socket 64, with the annular flange 34 of the pin 12 engaged with the distal end 62 of the elongated shaft 42.

Figure 4:
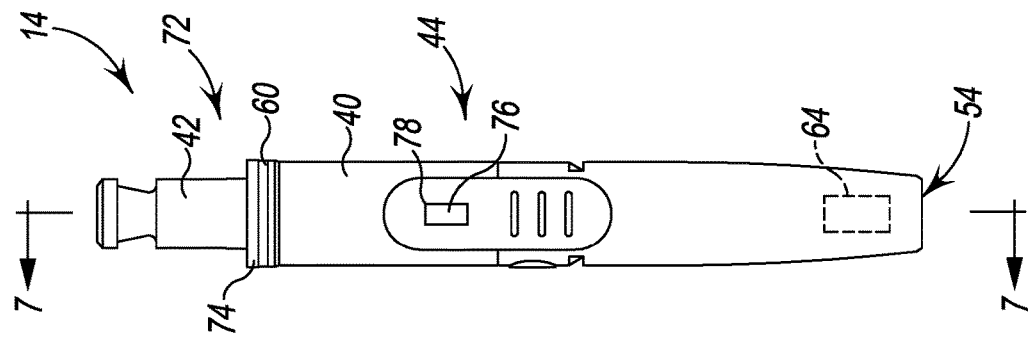
FIG. 4 is a side elevation view similar to FIG. 3.
Figure 3:
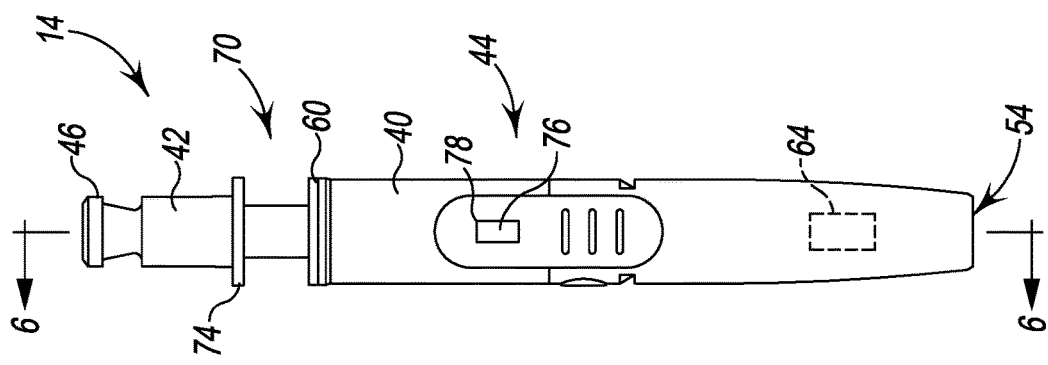
FIG. 3 is a side elevation view of the surgical instrument of FIG. 2.

As described above, the shaft 42 is moveable relative to the sheath 40. As shown in FIGS. 3 and 4, the shaft 42 is moveable between a controlled-torque position 70 (see FIG. 3) and a full torque position 72 (see FIG. 4). In the controlled-torque position 70, the distal flange 74 of the shank 46 is spaced apart from the proximal end 60 of the sheath 40, and the socket 64 is spaced inwardly from the distal opening 54 of the sheath 40. In the full torque position 72, the distal flange 74 of the shank 46 is engaged with the proximal end 60 of the sheath 40. Additionally, the socket 64 is positioned adjacent the distal opening 54 of the sheath 40.

In the illustrative embodiment, the locking mechanism 44 includes a locking tab 76 that is configured to be received in a slot 78 defined in the sheath 40 when the shaft 42 is in a controlled-torque position 70. The engagement between the locking tab 76 and the sheath 40 fixes the sheath 40 and the shaft 42 in position relative to one another, as described in greater detail below.

Figure 5:
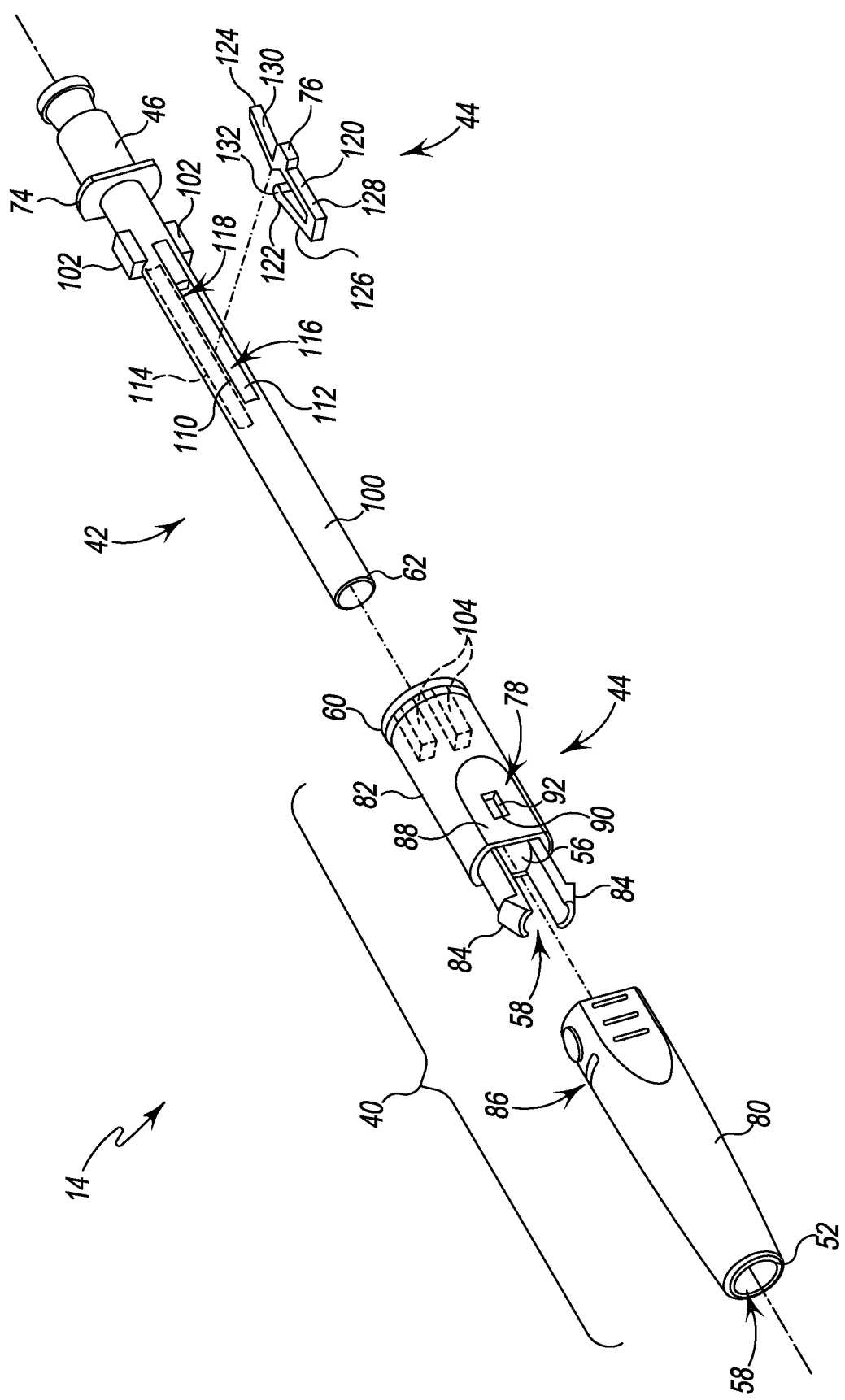
FIG. 5 is an exploded perspective view of the surgical instrument of FIG. 2.

Referring now to FIG. 5, the sheath 40, shaft 42, and locking mechanism 44 are shown in greater detail. In the illustrative embodiment, the sheath 40 is an assembly of two components 80, 82. It should be appreciated that in other embodiments the sheath 40 may be formed as a single monolithic component. The component 80 is positioned distally and defines the distal end 52 of the sheath 40. The other component 82 includes the proximal end 60 of the sheath 40. A pair of flanges 84 extend distally from the component 82 and are configured to engage a corresponding pair of slots 86 defined in the component 80 to secure the components 80, 82 and assemble the sheath 40.

The proximal component 82 includes a substantially planar surface 88, and a generally rectangular opening 90 is defined in the surface 88. A number of inner walls 92 extend inwardly from the opening 90 to define the locking slot 78 described above. As shown in FIG. 5, the locking slot 78 opens into the central passageway 58, which extends through both the components 80, 82 of the sheath 40.

As described above, the elongated shaft 42 has a distal end 62 that is positioned in the central passageway 58 of the sheath 40. A substantially cylindrical surface 100 extends from the distal end 62 to the drive shank 46 formed at the proximal end 48 of the shaft 42. In the illustrative embodiment, a pair of tabs 102 extends outwardly from the surface 100 near the drive shank 46. Each tab 102 is received in a guide slot or groove 104 defined in the inner wall 56 of the proximal component 82. The tabs 102 and grooves 104 cooperate to guide the relative movement of the shaft 42 and sheath 40 and prevent relative rotation between the shaft 42 and the sheath 40.

Figure 6:
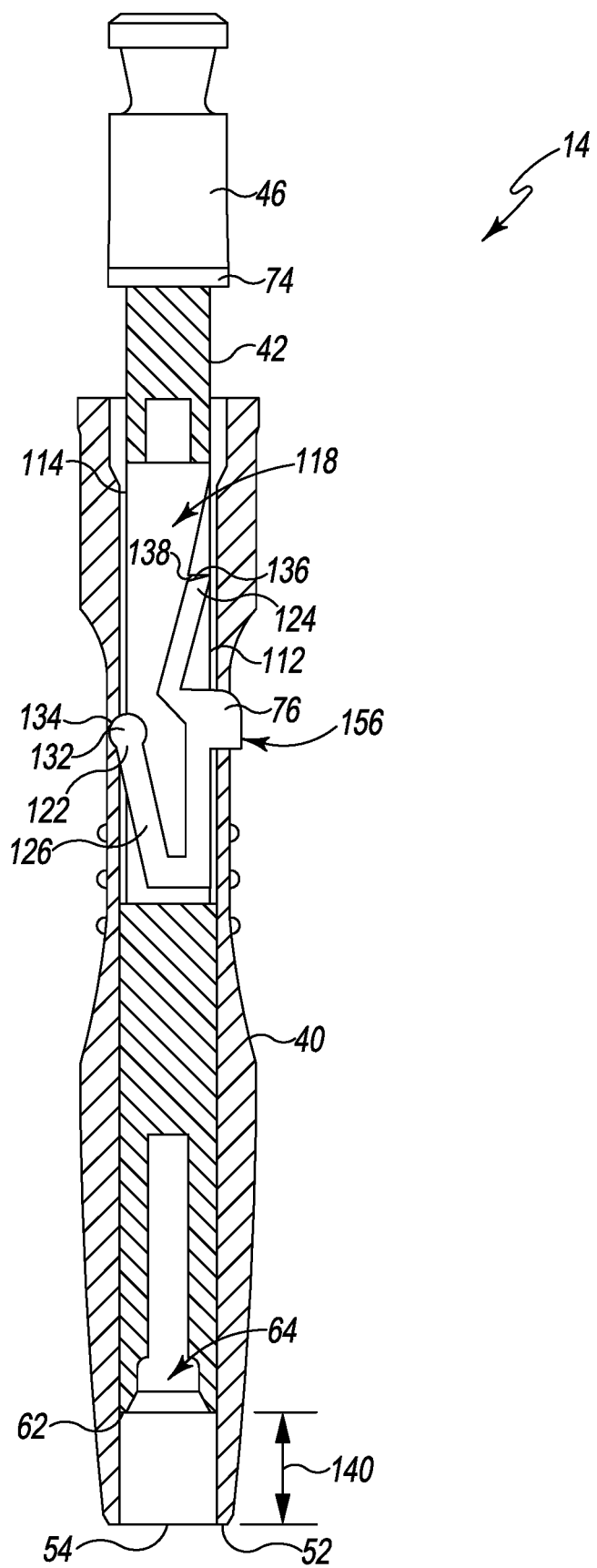
FIGS. 6 and 6A are cross section views of the surgical instrument taken along the line 6-6 in FIG. 3, with FIG. 6A showing a pin with the surgical instrument.
Figure 6A:
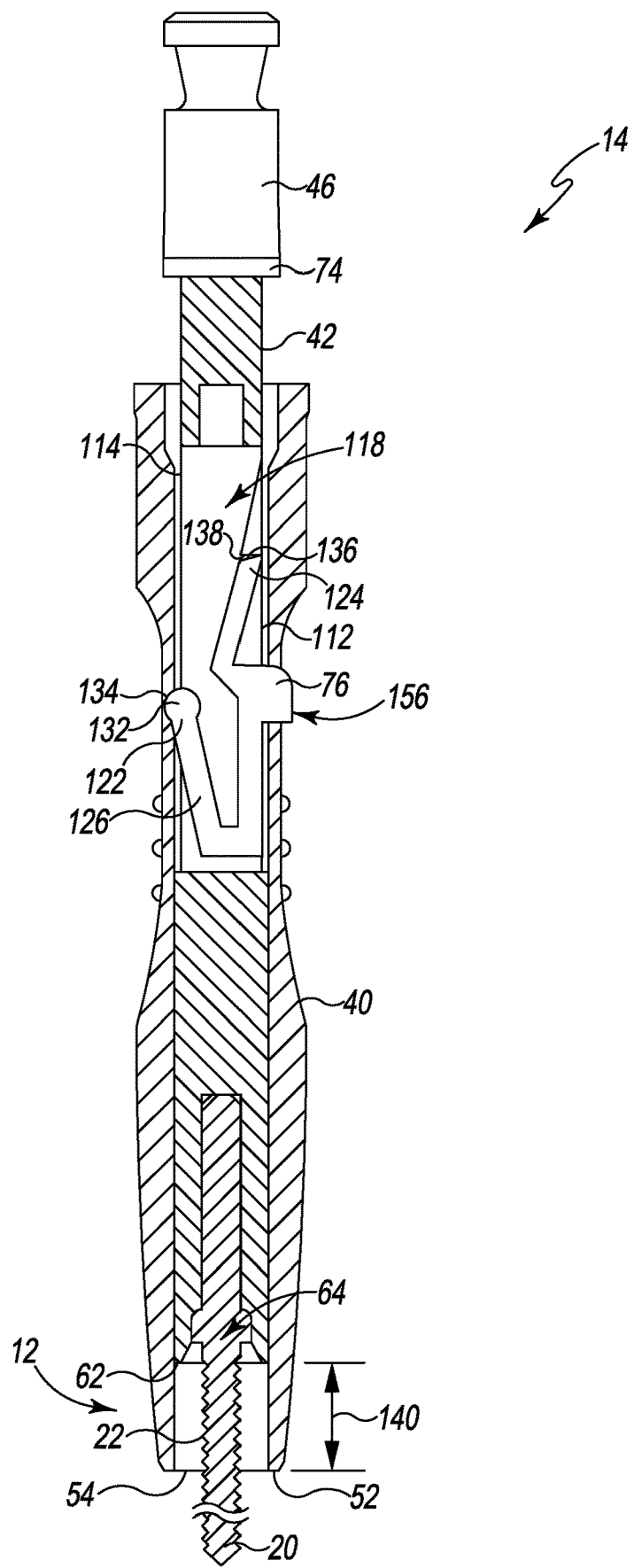

The shaft 42 has a longitudinal opening 110 defined in the cylindrical surface 100. A number of inner walls 112 extend inwardly from the opening 110 to another longitudinal opening 114 defined in the opposite side of the surface 100 to define a slot 116 extending through the shaft 42, as shown in FIG. 6. The walls 112 further cooperate to define an inner chamber 118 positioned proximal of the slot 116. The slot 116 and inner chamber 118 are sized to receive the lever 120 of the locking mechanism 44.

Returning to FIG. 5, the locking mechanism 44 has a lever 120 and the locking tab 76 described above. The lever 120 extends from an end 122 that engages the sheath 40 to another lever end 124 that engages the elongated shaft 42. The lever 120 includes an arm 126 that extends from the lever end 122 and is joined at its opposite end to a body 128. The body 128 connects the arm 126 to another arm 130 that extends from the lever end 124. The locking tab 76 extends outwardly from the connecting body 128. In the illustrative embodiment, the lever 120 and locking tab 76 are formed as a single monolithic component from a resilient material such as, for example, spring steel.

As shown in FIG. 6, the arm 126 has a lip 132 formed at the lever end 122 that is received in a groove 134 defined in the inner wall 56 of the proximal component 82 of the sheath 40. The arm 130 has a substantially planar or flat surface 136 at the opposite lever end 124, which is configured to engage a distal-facing surface 138 of the elongated shaft 42.

In use, the elongated shaft 42 of the fixation pin driver 14 is positioned in the controlled-torque position 70 shown in FIGS. 3 and 6. In that position, the surface 136 of the locking mechanism lever 120 is engaged with the distal-facing surface 138 of the elongated shaft 42 and the locking tab 76 is positioned in the slot 78 defined in the sheath 40. As shown in FIG. 6, the distal end 62 of the elongated shaft 42 (and hence the socket 64) is spaced apart from the distal opening 54 of the sheath 40 such that a distance 140 is defined between the opening 54 and the distal end 62 and socket 64 of the elongated shaft 42.

A user may load a bone fixation pin 12 into the driver 14 by aligning the head 16 of the pin 12 with the distal opening 54 of the sheath 40. The user may then advance the head 16 of the pin 12 into the distal opening 54, along the central passageway 58, and into the socket 64 of the elongated shaft 42. As described above, the annular flange 34 of the pin 12 engages the distal end 62 of the elongated shaft 42 when the head 16 is fully seated in the socket 64. With the head 16 fully seated in the socket 64, a number of the threads 22 of the pin 12 are positioned in the central passageway 58 of the sheath 40 because the distance 140 is greater than the distance 36 defined between the distal edge 30 of the head 16 and the proximal edge 24 of the threads 22.

Figure 7:
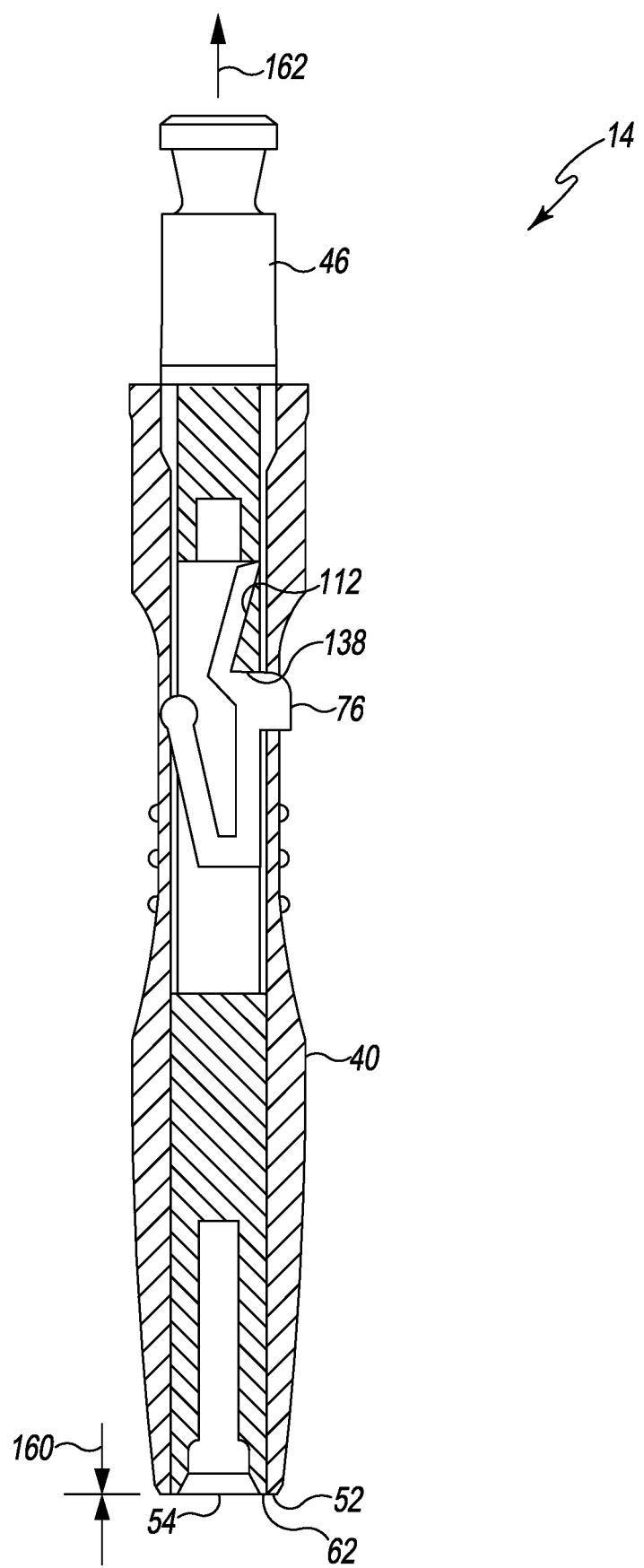
FIGS. 7 and 7A are cross section views of the surgical instrument taken along the line 7-7 in FIG. 4, with FIG. 7A showing a pin with the surgical instrument.
Figure 7A:
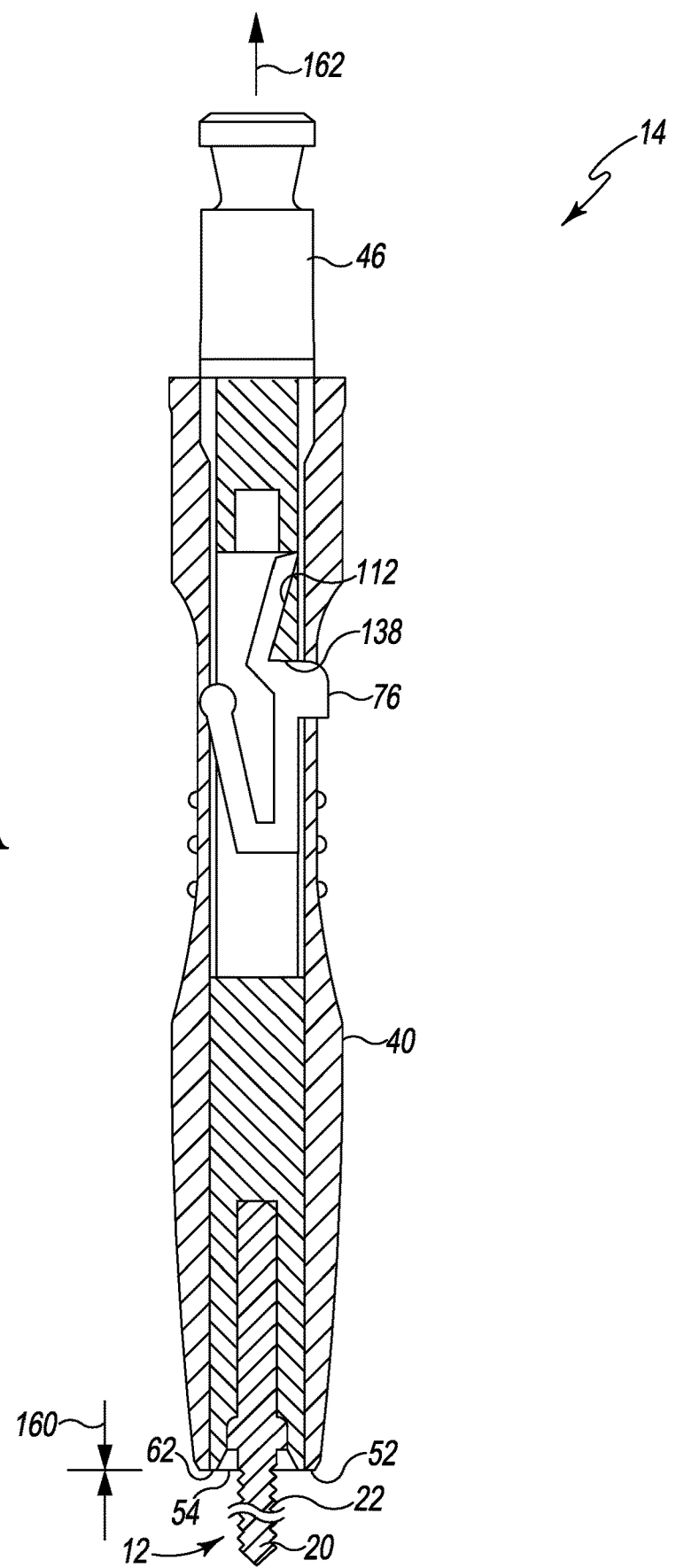
Figure 8:
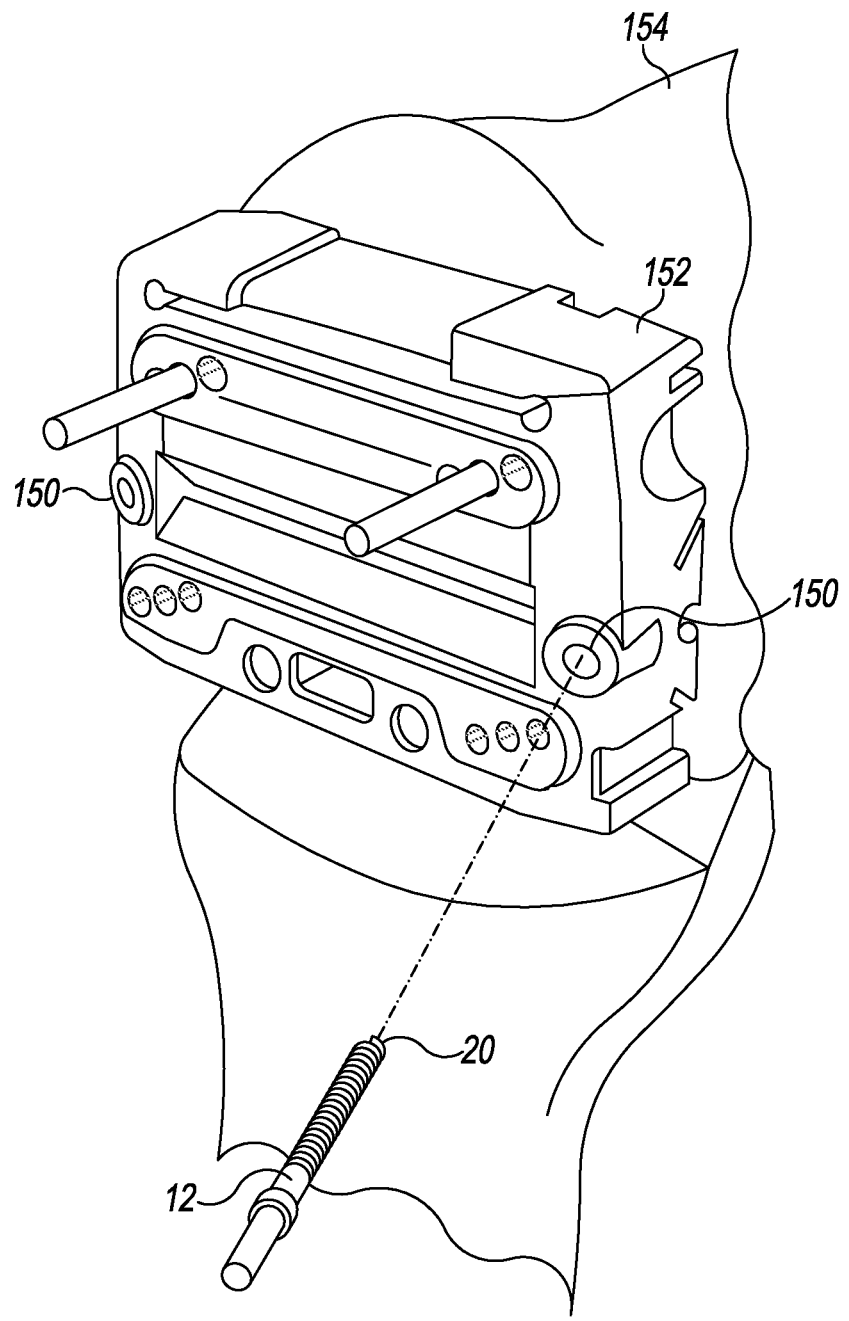
FIG. 8 is a perspective view of a cutting block positioned on a patient's bone and a bone fixation pin of the surgical instrument system of FIG. 1.
Figure 9:
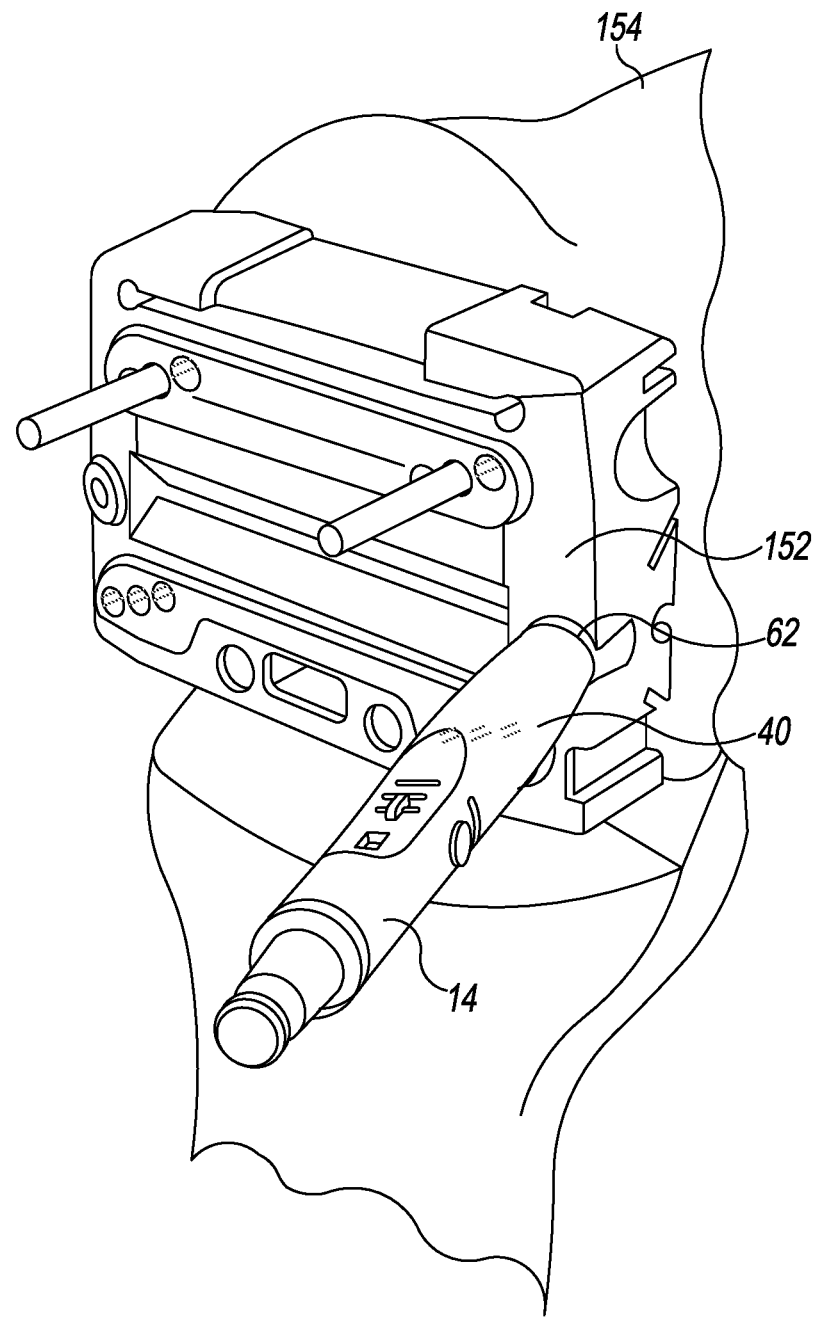
FIG. 9 is a perspective view similar to FIG. 8 showing the surgical instrument system of FIG. 1 used to secure the cutting block to the patient's bone.
Figure 10:
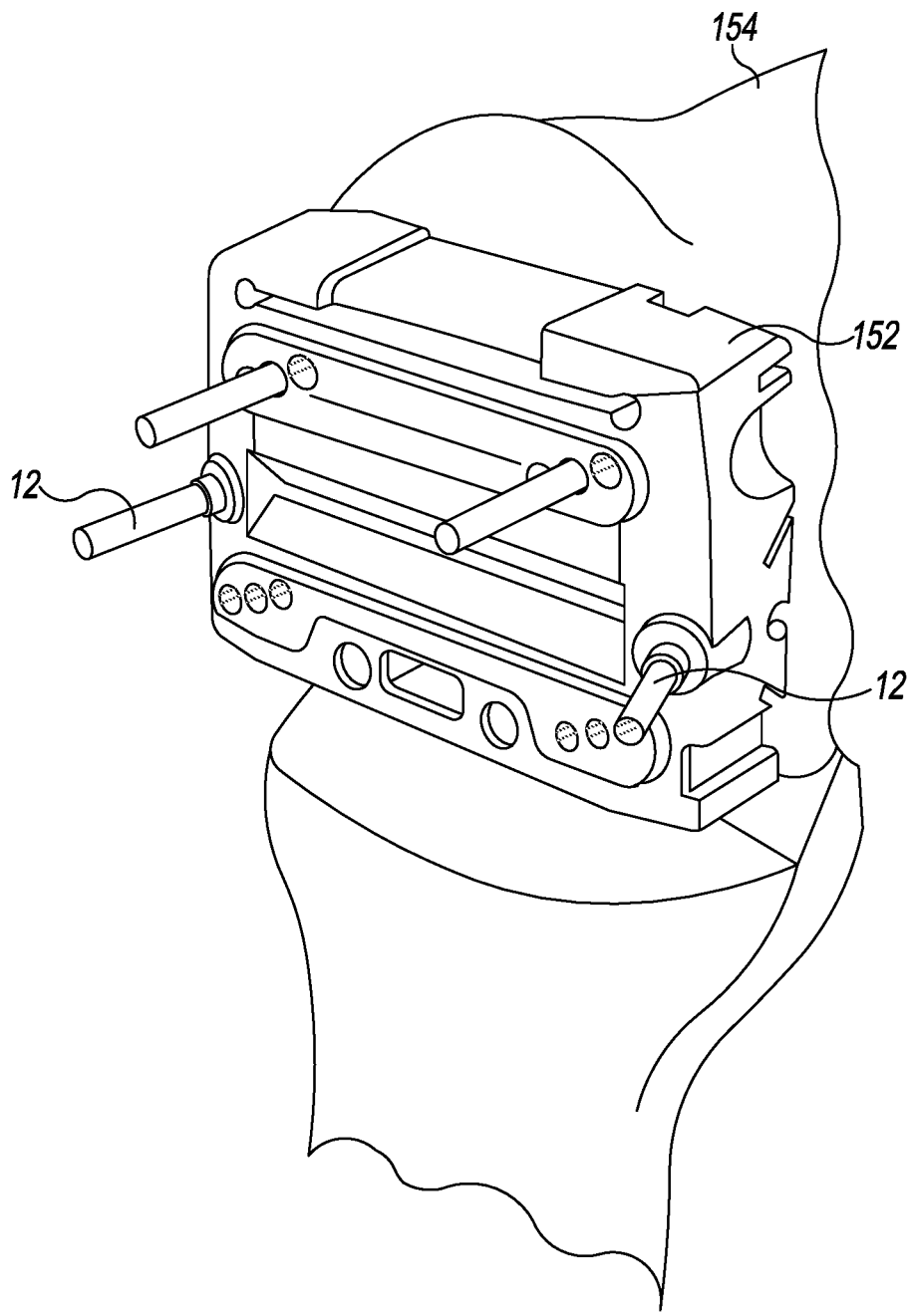
FIG. 10 is a perspective view similar to FIG. 8 showing the cutting block attached to the patient's bone with a pair of bone fixation pins.

As shown in FIG. 7, the user may align the distal tip 20 of the pin 12 with a guide pin hole 150 of a surgical instrument such as, for example, femoral cutting block 152, to be secured to the patient's bone 154. In other embodiments, the surgical instrument may be a tibial cutting block, a sizing block, gauge, or other surgical instrument. The user may then advance the distal tip 20 into the hole 150 and into contact with the patient's bone 154. As described above, a surgical drill or other rotary power tool may be attached to the drive shank 46 to rotate the driver 14 (and hence the fixation pin 12) to screw the pin 12 into the patient's bone 154. As the driver 14 is rotated about its axis 50, the pin 12 advances into the patient's bone 154, and the distal end 62 of the sheath 40 is advanced into contact with the cutting block 152, as shown in FIG. 9.

When the distal end 62 of the sheath 40 contacts the cutting block 152, further movement of the driver 14 toward the patient's bone 154 is prevented. However, continued rotation of the driver 14 causes the pin 12 to continue to advance into the patient's bone 154. As the pin 12 advances, the head 16 of the pin 12 is advanced distally, away from the socket 64. With continued rotation of the driver 14, the head 16 is advanced out of engagement with the socket 64. The sheath 40 is sized so that the head 16 is advanced out of engagement with the socket 64 to prevent the user from applying too great a torque to the pin 12.

If the user desires to further tighten the pin 12 or remove the pin 12, the user may depress the locking tab 76 by applying a force in the direction indicated by arrow 156 in FIG. 6. When the locking tab 76 is disengaged from the slot 78, the user may advance the elongated shaft 42 along the longitudinal axis to the full torque position 72 shown in FIG. 7. When the user releases the locking tab 76, the lever 120 urges the tab 76 back into the slot 78, as shown in FIG. 7. In full torque position 72, the distal end 62 of the elongated shaft 42 (and hence the socket 64) is positioned adjacent to the distal opening 54 of the sheath 40 such that a distance 160 is defined between the opening 54 and the distal end 62 and socket 64 of the elongated shaft 42. The distance 160 is less than the distance 36 defined between the distal edge 30 of the fixation pin head 16 and the proximal edge 24 of the threads 22 such that the user may apply the full torque of the surgical drill to the fixation pin 12. In that way, additional torque may be applied to the pin 12 to further tighten the pin or remove the pin 12 from the bone.

To return the elongated shaft 42 to the controlled-torque position 70, the user may pull on the shank 46 as indicated by arrow 162. The arm 130 of the lever 120 slides along the inner wall 112 of the elongated shaft 42 until it reengages the distal-facing surface 138 in the controlled-torque position 70.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of attaching a surgical instrument to a patient's bone, the method comprising:
   positioning the surgical instrument in a desired location relative to the patient's bone,
   positioning a fixation pin driver in a controlled-torque position in which a socket defined in an elongated shaft of the fixation pin driver is positioned within a sheath of the fixation pin driver at a position in which the socket is spaced apart proximally from a distal opening of the sheath of the fixation pin driver by a first distance,
   inserting a head of a bone fixation pin through the distal opening of the sheath of the fixation pin driver into the socket defined in the elongated shaft of the fixation pin driver, wherein (i) the head of the bone fixation pin extends from a proximal end of the bone fixation pin to a distal edge, (ii) a shaft of the bone fixation pin has a plurality of the threads defined therein and extends from the distal end of the bone fixation pin to a proximal edge, (iii) a second distance is defined between the distal edge of the head and the proximal edge of the threads, (iv) the first distance is greater than the second distance such that a number of the threads of the bone fixation pin are positioned in a central passageway of the sheath of the fixation pin driver when the fixation pin driver is positioned in its controlled-torque position and the head of the bone fixation pin is seated in the socket of the elongated shaft,
   positioning the threaded distal end of the bone fixation pin in a guide hole defined in the surgical instrument,
   rotating the fixation pin driver, with the fixation pin driver positioned in its controlled-torque position, to thread the bone fixation pin into the patient's bone,
   engaging a distal end of the fixation pin driver with an outer surface of the surgical instrument,
   moving a locking mechanism of the fixation pin driver from a locked position in which a tab extending outwardly from a body of the locking mechanism that is positioned in a slot defined in the elongated shaft is positioned in an opening of the sheath to prevent movement of the elongated shaft within the sheath to an unlocked position in which the tab is spaced apart from the opening of the sheath to release the elongated shaft of the fixation pin driver for movement relative to the sheath of the fixation pin driver,
   moving the socket of the elongated shaft distally within the sheath toward the distal opening of the sheath so as to position the fixation pin driver in a full-torque position in which the socket of the elongated shaft is spaced apart from the distal opening of the sheath by a third distance, the third distance being less than the second distance, and
   rotating the elongated shaft of the fixation pin driver, with the fixation pin driver positioned in its full-torque position, to transfer torque from the socket to the head of the bone fixation pin to further thread the bone fixation pin into the patient's bone.

2. The method of claim 1, further comprising securing a proximal end of the elongated shaft to a surgical drill.

3. The method of claim 1, wherein:
   the surgical instrument is a cutting guide block, and
   positioning the surgical instrument in the desired location relative to the patient's bone comprises positioning the cutting guide block in the desired position relative to the patient's bone.

4. The method of claim 1, further comprising engaging an annular flange of the bone fixation pin with the outer surface of the surgical instrument after rotation of the elongated shaft of the fixation pin driver positioned in its full-torque position.

5. The method of claim 1, wherein moving the locking mechanism of the fixation pin driver from the locked position comprises pressing the tab of the locking mechanism to overcome a bias of a biasing element of the locking mechanism.

* * * * *